(12) United States Patent
Wallenas et al.

(10) Patent No.: US 7,976,709 B2
(45) Date of Patent: Jul. 12, 2011

(54) SYSTEM AND METHOD FOR REGENERATION OF A FLUID

(75) Inventors: Anders Wallenas, Lomma (SE); Lars Wramner, Molndal (SE)

(73) Assignee: Triomed AB, Lund (SE)

( * ) Notice: Subject to any disclaimer, the term of this patent is extended or adjusted under 35 U.S.C. 154(b) by 266 days.

(21) Appl. No.: 11/884,353

(22) PCT Filed: Feb. 16, 2006

(86) PCT No.: PCT/SE2006/000212
§ 371 (c)(1),
(2), (4) Date: Sep. 23, 2008

(87) PCT Pub. No.: WO2006/088419
PCT Pub. Date: Aug. 24, 2006

(65) Prior Publication Data
US 2009/0114595 A1    May 7, 2009

(30) Foreign Application Priority Data
Feb. 16, 2005  (SE) ..................... 0500369

(51) Int. Cl.
*C02F 9/00* (2006.01)
*B01D 11/00* (2006.01)
(52) U.S. Cl. ........ 210/645; 210/646; 210/652; 210/772; 210/791; 210/259
(58) Field of Classification Search ........... None
See application file for complete search history.

(56) References Cited

U.S. PATENT DOCUMENTS

| 3,839,200 A | 10/1974 | Gigou et al. |
|---|---|---|
| 3,926,797 A | 12/1975 | Gigou et al. |
| 4,269,708 A | 5/1981 | Bonomini et al. |
| 2004/0019312 A1* | 1/2004 | Childers et al. ............. 604/4.01 |
| 2004/0182787 A1 | 9/2004 | Chevallet et al. |

FOREIGN PATENT DOCUMENTS

| JP | 56-28570 | 7/1981 |
|---|---|---|
| JP | 62-14861 | 1/1987 |
| JP | 7-313589 | 12/1995 |
| JP | 10-71201 | 3/1998 |
| JP | 2003-510103 | 3/2003 |
| RU | 2 229 900 | 11/2003 |
| WO | WO 99/42150 | 8/1999 |
| WO | 2004/082733 | 9/2004 |

* cited by examiner

*Primary Examiner* — Krishnan S Menon
*Assistant Examiner* — Allison Gionta
(74) *Attorney, Agent, or Firm* — Capitol City TechLaw

(57) ABSTRACT

A system comprising a blood circuit including a membrane arranged in a blood filter (7) in which blood is in contact with a first side of said membrane; and a dialysis circuit in which a dialysis fluid is in contact with the other side of the membrane for exchange of substances and ions through the membrane as well as water. The dialysis fluid is circulated from a dialysis compartment and through a RO filter (9). The permeate fluid, i.e. water is returned to the dialysis compartment. The retentate fluid from the RO filter (9) passes through a separation filter (13). The retentate fluid is returned to the dialysis compartment and the permeate fluid is removed from the dialysis circuit as a waste fluid to a receptacle (19). The retentate fluid is concentrated in the RO filter in a ration of at least 3:1.

11 Claims, 15 Drawing Sheets

SYSTEM AND METHOD FOR REGENERATION OF A FLUID

AREA OF INVENTION

The present invention relates to a method and system for regeneration of a fluid for a blood purification system for removal of soluble products from a body fluid, which is arranged to be permanently connected to a patient and being portable so that the patient can bring the system with himself. The system is particularly intended for removal of waste products from the blood of a patient having impaired or no kidney function.

BACKGROUND OF INVENTION

Patients having impaired or no kidney function are normally treated by dialysis. Hemodialysis may take place e.g. during four hours each second day. During hemodialysis, the blood of the patient is circulated in an extra-corporeal circuit and passed through a dialysator having a semipermeable membrane, one side of which being in contact with the blood. The other side of the semipermeable membrane is in contact with a dialysis fluid having a certain composition. Waste products such as urea and creatinine may pass from the blood through the membrane to the dialysis fluid by means of diffusion driven by a concentration gradient. Other solutes, such as bicarbonate may pass the other way from the dialysis fluid through the membrane to the blood, e.g. to counteract acidification of the patient. Fluid is removed from the blood of the patient through the membrane. The dialysis fluid is normally discarded after the treatment. During a dialysis treatment of four hours, often several hundred liters of dialysate are used. Such a treatment normally takes place on a dialyse centre under the supervision of trained personnel.

Recently, dialysis machines have been produced intended for home use, wherein another person of safety reasons normally assists the patient. Online monitoring makes it possible to control or supervise the operation from a hospital. Such home-based dialysis can take place more often. The home dialysis treatment makes it possible to perform dialysis every day or even two times per day.

The drawback with conventional hemodialysis, as described above, is that the waste products accumulate between the treatments and the body is exposed to highly varying concentrations of e.g. urea and creatinine in the body fluids. Moreover, the patient cannot get rid of excess fluid between the treatments, which results in that the weight of the patient varies e.g. 4 kg between the treatments. In this case, 4 l of fluid may be removed from the patient during each treatment. This varying concentration of substances and load of fluid may be harmful for the patient and a more continuous hemodialysis treatment will be advantageous.

Thus, there is a need for a hemodialysis treatment, which may be performed continuously, which means that the dialysis system has to be portable so that the user can live a normal life.

Such a portable hemodialysis apparatus is shown e.g. in U.S. Pat. No. 4,269,708. The apparatus comprises a dialysator connected to the patient via conventional needles or catheters. The dialysator is also connected to a dialysis circuit having a vessel for clean dialysis liquid having a size of about 10 l. It is realised that this dialysis equipment is rather heavy but it is possible to carry it, e.g. as a backpacker. A smaller vessel may be connected for decreasing the weight temporarily. The device also comprises filters for removing toxic components such as an active carbon filter. Fluid is withdrawn from the blood in an ultrafiltration process and directly discarded to a receptacle. The apparatus according to U.S. Pat. No. 4,269,708 is, however, too heavy to be convenient to carry all the time. Thus, there is a need for a dialysis system, which is small and may be connected to the patient continuously. The system should be wearable and not too heavy.

DISCLOSURE OF INVENTION

An object of the invention is to provide a method and a system for regeneration of a fluid for blood purification for continuous use and being sufficiently light to be able to be carried every day.

In a first aspect, there is provided a system for regeneration of a fluid included in a compartment and being in contact with blood via a membrane and/or being filtered from blood comprising: a device for providing said fluid from said compartment to a filtering device for filtering substantially only water from said fluid for providing a concentrated fluid; a device for removing at least a portion of said concentrated fluid; and a device for returning the non-removed portion and said water as said regenerated fluid to said compartment and/or directly to the blood. The concentrated fluid of said filtering device may be concentrated at least in a ratio of 3 to 1, such as 10 to 1, for example 15 to 1.

In an embodiment, the compartment may be the abdominal cavity of a patient and said membrane is a peritoneal membrane in the abdominal cavity.

The system may further comprise a separating filter connected to the retentate outlet of said filtering device, whereby a retentate fluid of said separating device is returned to said compartment and a permeate fluid of said separating device is removed from the system as a waste fluid. The separating filter may be a filter system comprising at least two separating membranes.

In an embodiment, the system may comprise: a first pump for passing said fluid from said compartment to said filtering device; a second pump for passing a retentate fluid from said filtering device to said separating filter; and a third pump for passing a permeate fluid from the separating filter to a receptacle as a waste fluid. Alternatively, the system may comprise: a first pump for passing said fluid from the compartment to said filtering device; a second adjustable valve for passing a retentate fluid from said filtering device to said separating filter; and a third pump for passing a permeate fluid from said separating filter to a receptacle as a waste fluid.

In another embodiment, the system may comprise a port arranged in a blood circuit including said membrane and compartment, said port being connected for passing at least a portion of said regenerated fluid into the blood circuit before said compartment, so called predilution. Alternatively, said port may be connected for passing at least a portion of said regenerated fluid into the blood circuit after said compartment, so called postdilution.

In a further embodiment, the system may comprise a separating filter being connected between said compartment and said filtering device, whereby a retentate fluid of said filtering device is returned to said compartment and a permeate fluid of said filtering device is passed to said filtering device for concentration and removal from the system as a waste fluid.

In a still further embodiment, the system may comprise an ultrafiltration filter connected to a retentate outlet of said filtering device, the permeate of said ultrafiltration filter being returned to said compartment and the retentate of said ultrafiltration filter being passed to said filtering device for concentration. Each pump arranged immediately before the inlet of said filtering device may be a powerful pump arranged for providing a pressure sufficient for passing substantially only water through the membrane of the filtering device. A valve may be connected to the retentate outlet of said separation filter for directing the outlet fluid to said ultrafiltration filter and/or to said compartment. A circulation pump may be arranged between the inlet and the retentate outlet of any one of said separation filter, said ultrafiltration filter and said filtering device, for increasing the tangential flow of fluid over said membrane of each filter.

In another aspect, there is provided a method for regenerating a fluid included in a compartment and being in contact with blood via a membrane and/or being filtered from blood, which method comprises the steps of: concentrating said fluid by means of a filtering device to form a concentrated fluid and a permeate fluid which is substantially only water; returning said permeate fluid to said compartment and/or directly to the blood; and removing at least a portion of said concentrated fluid as a waste fluid.

Some advantages obtained with one or several of the aspects and embodiments mentioned above are:
  decreasing the dialysis time;
  re-utilizing the dialysate;
  more freedom to the patient;
  increased utilization of clinics and personnel;
  reduced costs;
  simple to operate;
  simple in construction;
  easily obtained from commonly available components;
  requires no special or complex maintenance;
  continuous treatment makes the patient feel better.

BRIEF DESCRIPTION OF DRAWINGS

Further objects, features and advantages of the invention will appear from the description below of embodiments of the invention with reference to the drawings, in which.

DETAILED DESCRIPTION OF EMBODIMENTS

Figure 1:
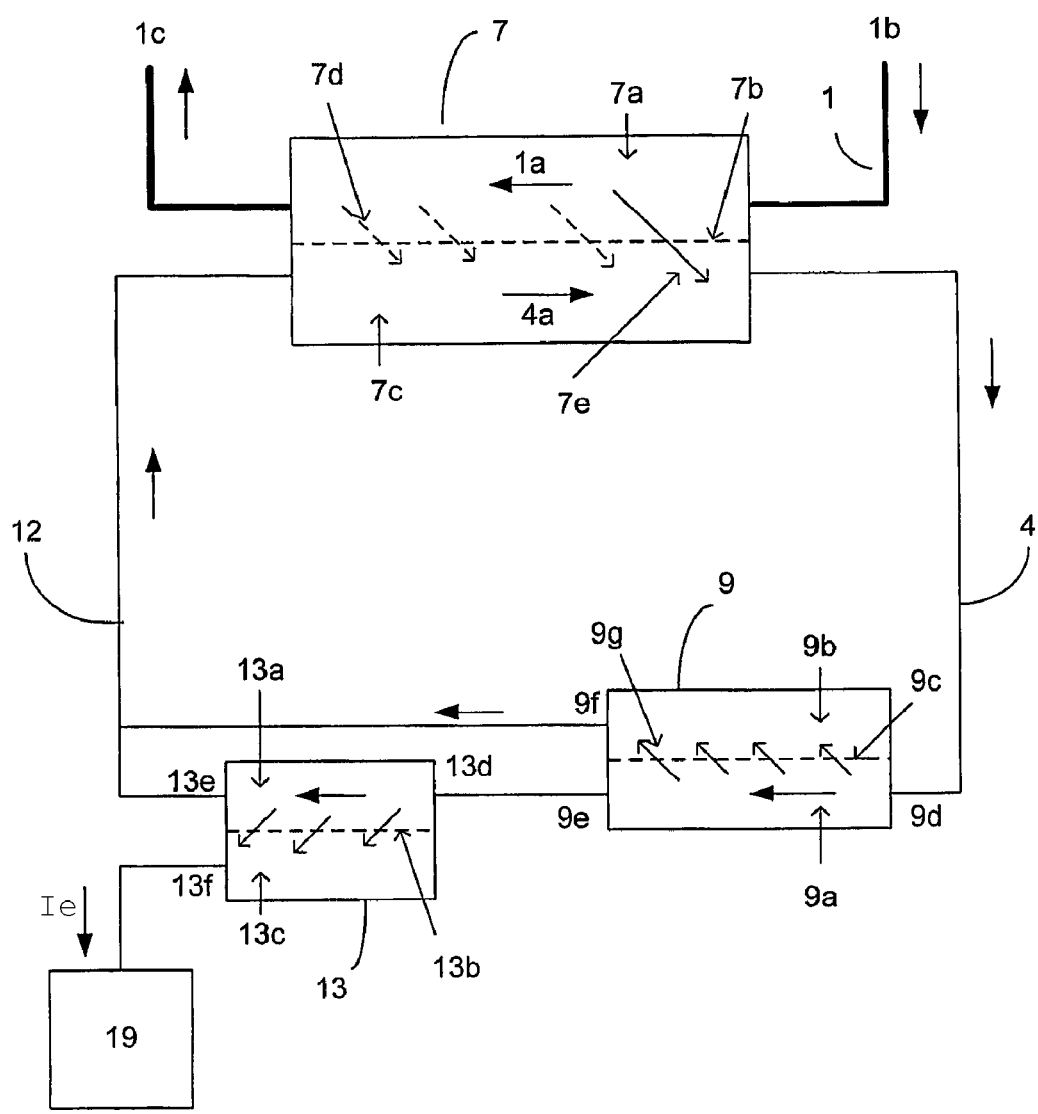
FIG. 1 is a schematic view of an embodiment of the invention.

An embodiment of a fluid regeneration system for blood purification is shown in FIG. 1. The system comprises a blood filter 7, which is an ultrafilter or dialysator, comprising a blood compartment 7a and a dialysate compartment 7c separated by a semipermeable membrane 7b. In the blood compartment 7a, blood is circulated through a blood circuit 1 as shown by arrow Ia. Dialysate or dialysis fluid is circulated in the dialyser compartment 7c as shown by arrow 4a, normally in a counterflow.

Blood circuit 1 may comprise a first needle or catheter connected to inlet line Ib and a second needle or catheter connected to outlet line Ic. The needles or catheters may be inserted in blood vessels or a single blood vessel of the mammal being treated by the system. The needles may be inserted in a fistula arranged in the arm of a patient. Alternatively, catheters may be inserted in suitable arteries and/or veins of the patient. In the case a first catheter is inserted in the artery and a second catheter is inserted in a vein, the difference in pressure between the artery and the vein may drive the blood in the blood circuit. The blood circuit may be extracorporeal as shown in FIG. 1. However, in certain embodiments, the dialyser may be surgically inserted in a patient more or less permanently. A pump may drive the blood in the extracorporeal circuit. Security devices as is common in hemodialysis may be used, such as air trap chambers, pressure monitors, etc.

On the dialysate compartment 7c of the membrane 7b, a dialysis fluid or dialysate is circulated as shown by arrow 4a. An exchange of ions will take place over the membrane as indicated by arrows with broken lines 7d. This transport of ions and substances is driven by the concentration gradient over the membrane, normally from the blood to the dialysate. A small amount of fluid is also transported over the membrane as indicated by a solid line arrow 7e. The fluid flow in the blood circuit may be opposite to the fluid flow in the dialysate compartment, but flows in the same directions are also possible.

As substances are transported over the membrane, an equilibration of the concentrations of these substances between the blood in compartment 7a and the dialysate in compartment 7c will take place. Only the substances, which are sufficiently small to pass the membrane, will be equilibrated, while molecules and cells in the blood having a size, which is larger than the pores of the membrane, will be retained in the blood. If membrane 7b has a size exclusion of about 50 000 D, all smaller ions and substances will pass the membrane, while albumin and larger molecules and cells will be retained on the blood side of the membrane.

The dialysate circuit 4 further comprises a second filter 9. The dialysate from compartment 7c enters the second filter in a first compartment 9a. Filter 9 is arranged as a reverse osmosis or RO filter, which means that fluid enters the filter via an inlet 9d to a first compartment 9a, and leaves the filter as a retentate fluid through an outlet 9e and a permeate fluid through an outlet 9f after passing the filter membrane 9c as indicated by arrows 9g. The filter membrane is a membrane having very small pores and passing essentially only water.

The retentate is passed through outlet 9e to an inlet 13d of a separation filter 13 having a first compartment 13a, a membrane 13b and a second compartment 13c. The retentate from the RO filter 9 enters the separation filter 13 via inlet 13d, and the retentate leaves the third filter via an outlet 13e and the permeate leaves the third filter via outlet 13f. The permeate is collected in a receptacle 19. Membrane 13b in filter 13 may have a pore size excluding molecules larger than about urea and creatinine. Thus, the permeate comprises water and smaller molecules such as urea, creatinine, $Na^+$, $K^+$, $Ca^{++}$ etc and possibly some glucose.

The retentate of filter 13 and the permeate of filter 9 are returned to the dialyser 7, via line 12. The dialysis fluid is driven and controlled in the dialysis circuit 4 by suitable pumps or throttles or valves as will be described in further detail below.

The operation of the dialysis circuit according to FIG. 1 is as follows: Waste products and other small substances and/or ions in the blood passes through membrane 7b of the blood filter 7 into the dialysis fluid as indicated by arrows 7d. The dialysis fluid is circulated into the RO filter 9 wherein essentially only water passes through the filter membrane 9c in order to concentrate the dialysis fluid present as retentate in the first chamber or compartment 9a. The concentrated dialysis fluid or retentate is passed to the separation filter 13 wherein a portion passes the filter membrane and leaves the system to the receptacle 19. Only ions having a size smaller than the exclusion size of the membrane in the separation filter is removed from the system. The remaining concentrated dialysate or retentate in the separation filter is combined with the water separated in RO filter 9 and returned to the dialyser 7. In this way, the dialysate entering the dialysate compartment 7c will have a low content of urea and creatinine (and other small ions) that has been separated by filter 13. Consequently, urea and creatinine is transferred from the blood to the dialysate as indicated by arrows 7d. Other ions like phosphate or other larger substances have not been removed by separation filter 13 and remain in the dialysate circuit. Thus, there is no concentration gradient between the blood and the dialysate for these larger substances and they will remain in the blood.

By removing a certain amount of fluid from the system to receptacle 19, a corresponding amount of fluid is taken out from the blood as indicated by arrow Ie. Such fluid may be approximately 1.5 l per day, which corresponds to the normal amount of urine excreted by a healthy human being. Since the system is closed, the system will be self-regulating. This removed fluid may be called artificial urine.

An advantage with the above system is that it makes it possible to use a very small amount of dialysis fluid in the circuit, in the order of a few liters or even less than one liter. Moreover, no new dialysis fluid is required but the circulating fluid is regenerated, such as constantly regenerated. The filters may be small, because they are used continuously.

For example, the dialysator or blood filter may have an active surface of 0.1 m$^2$ or smaller, the RO filter may have an active surface of 0.005 m$^2$ or smaller and the separation filter may have an active surface of 0.05 m$^2$ or smaller.

The blood flow may be less than 50 ml/min, such as less than 20 ml/min.

Thus, the complete system will be very small and can easily be worn by the patient all the time. As mentioned above, the advantage of the system is that it is essentially a continuous system, which may be operated all the time, or part of the time, at the option of the patient. It may be that the patient wants to switch off the system during the night, of one or the other reason.

The embodiment described above with reference to FIG. 1 is operated as a normal dialysis system using diffusion for transferring waste substances from the blood to the dialysate and using separation and concentration for removing waste substances from the dialysate fluid to a receptacle 19. Moreover, a concentration of the dialysate takes place in a RO filter before the separation filter.

Figure 2:
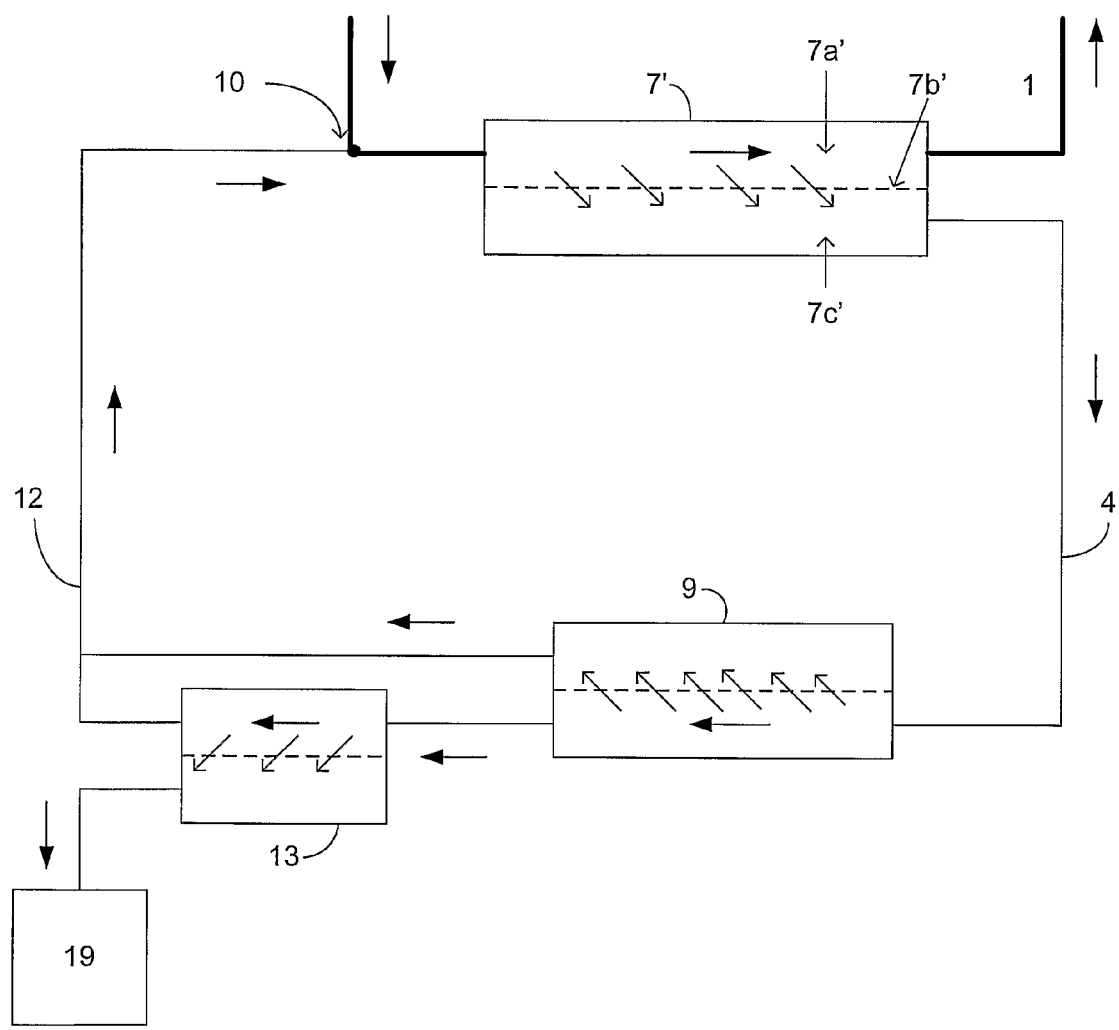
FIG. 2 is a schematic view of another embodiment, showing so called predilution.

In another embodiment, shown in FIG. 2, the dialysate circuit is arranged as a hemofiltration system. In this case, the first filter 7' is operated as an ultrafilter. This means that blood enters the dialysate and blood compartment 7a' and fluid passes through the membrane 7b' of the filter into the second compartment 7c'. The fluid is passed through the circuit 4 as before and is returned to the blood before the ultrafilter 7'. In this case, blood is diluted before entering the ultrafilter 7', which is called predilution.

Figure 3:
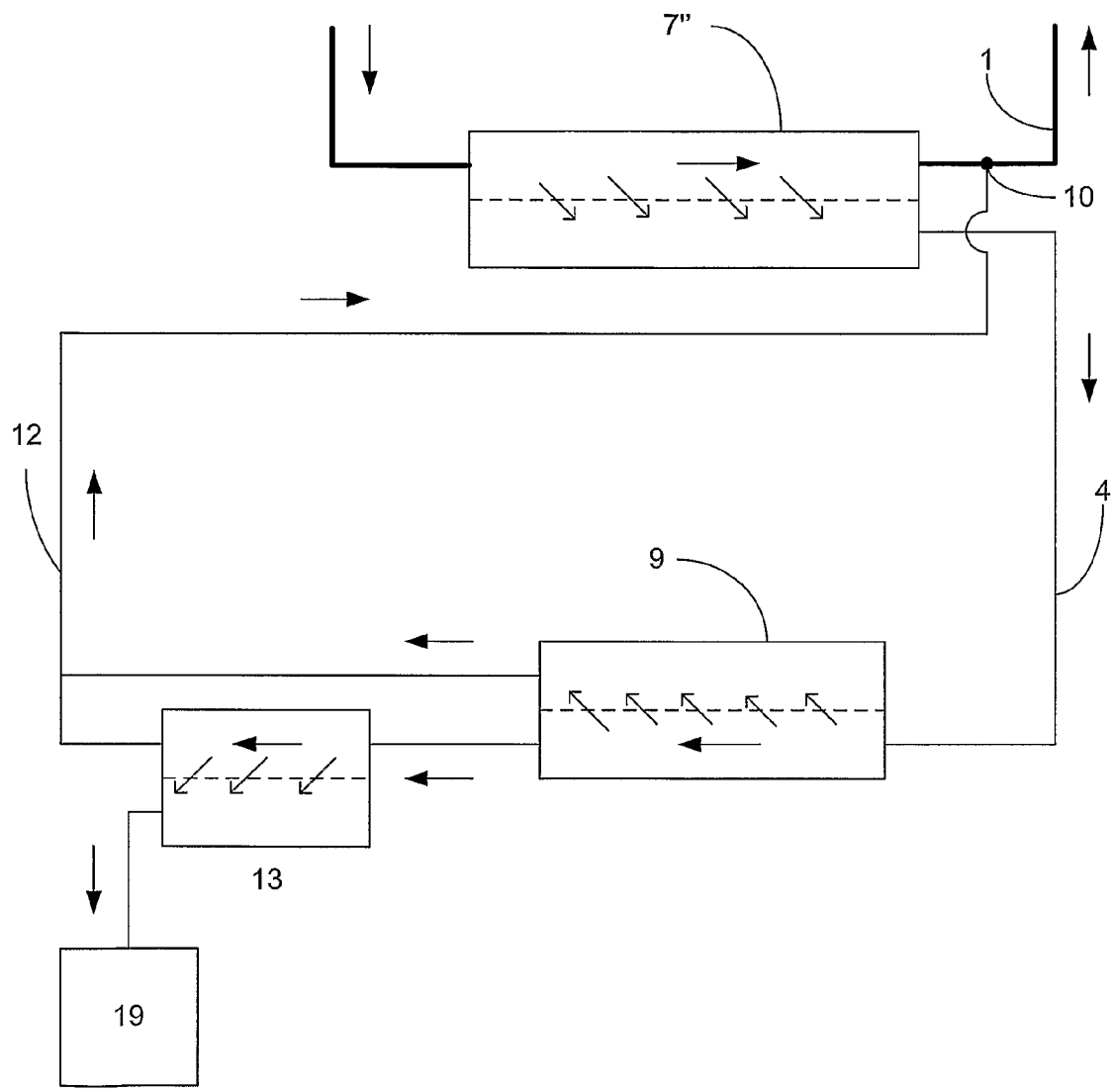
FIG. 3 is a schematic view of another embodiment, showing so called postdilution.

A further embodiment is shown in FIG. 3, which shows hemofiltration of the blood with postdilution of the blood. The operation is the same as described above, but blood is diluted after the ultrafilter 1".

Figure 4:
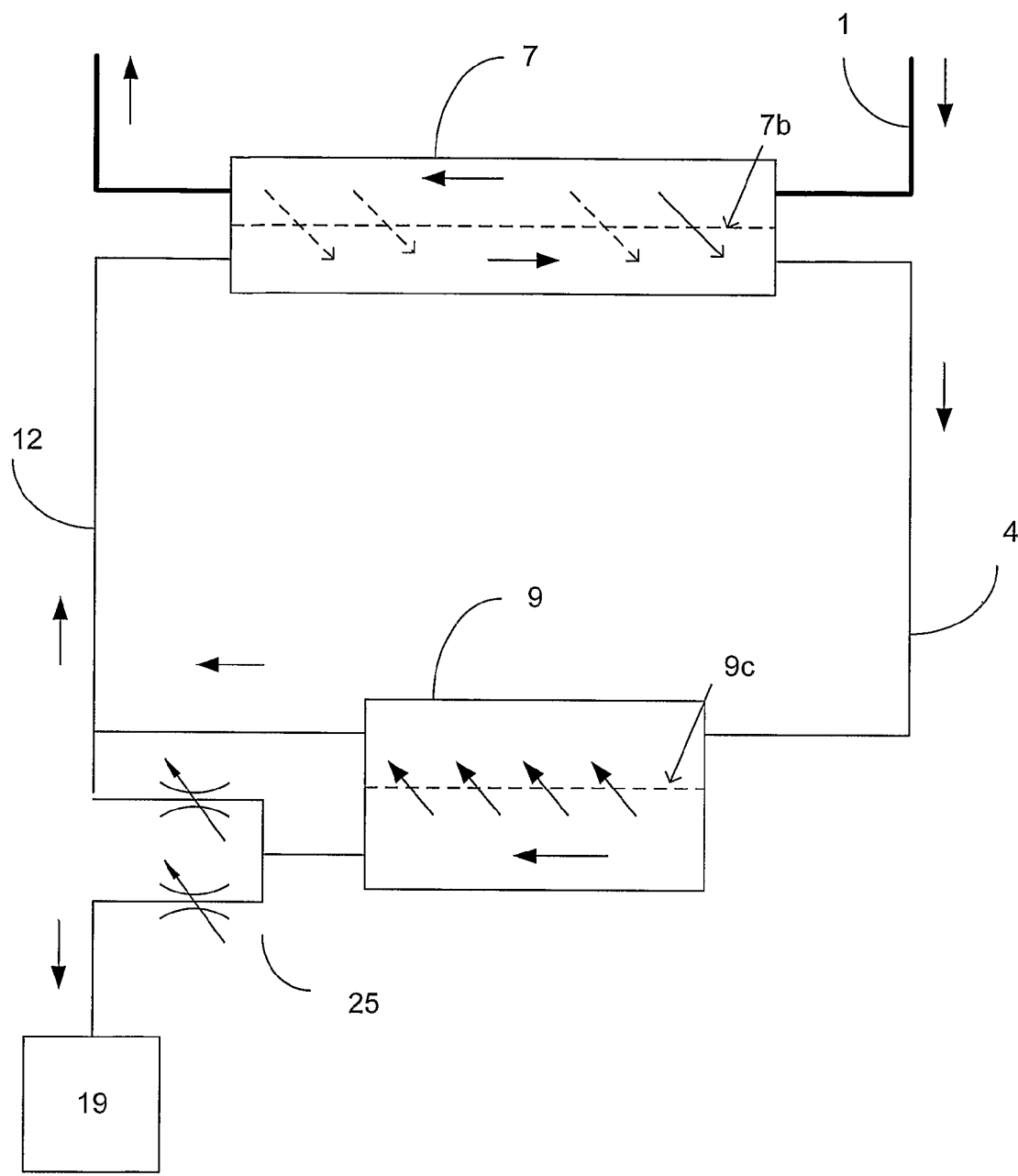
FIG. 4 is a schematic view of another embodiment.

FIG. 4 shows another embodiment differing from the embodiment of FIG. 1 by the fact that the third filter is replaced by a valve 25 arranged in the retentate outlet from RO filter 9. The valve 25 divides the outlet flow in a first portion directed to the receptacle 19 and a second portion returned to the dialyser 7 in combination with water obtained as filtrate from RO filter 9. Otherwise, the operation is the same as described above.

Membrane 7b in dialyser 7 in the embodiment of FIG. 4 may be a membrane having smaller pore size than in the previous embodiments, only passing substances and ions below a low size, e.g. below about 1000 D.

Figure 5:
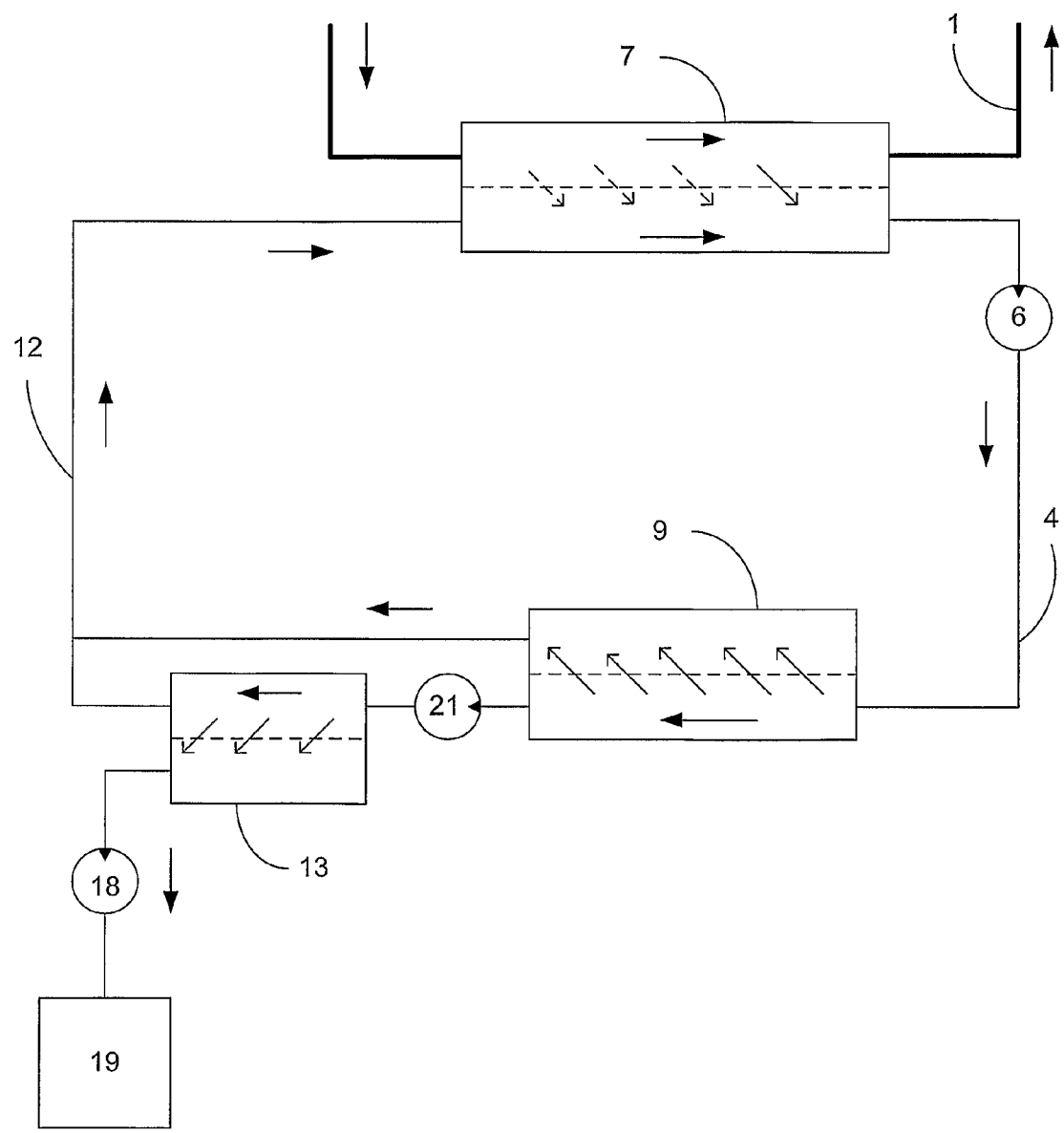
FIG. 5 is a schematic view of another embodiment provided with pumps and a separation filter.

FIG. 5 shows the embodiment according to FIG. 1 including pumps for operating the flows in the dialysis circuit 4. Thus, a first pump 6 is connected between dialyser 7 and the RO filter 9. A second pump 21 is connected between the RO filter 9 and the separation filter 13. A third pump 18 is connected between the separation filter 13 and the receptacle 19.

The pumps are operated e.g. as follows. The third pump 18 is adjusted so that a specific removal of fluid is performed as required by the patient for balancing input fluid, such as fluid which the patient has drunk and fluid included in the food ingested. Normally, between 1 and 2 l/day should be removed from a patient, which corresponds to approximately 1 ml/min. Thus, pump 18 is adjusted to 1 ml/min. The pump may be driven continuously or intermittently.

Pump 21 must be adjusted to a flow, which is larger than pump 18, e.g. about 2 ml/min. Pump 6 is adjusted so that a desired concentration of dialysis fluid is obtained in filter 9. If a concentration of ten times is desired, pump 6 is operated with a flow rate which is ten times that of pump 21, i.e. about 20 ml/min. The pump will develop a pressure suitable for passing 18 ml/min of water through the membrane and 2 ml/min as a retentate to the separation filter.

Since filter 9 is a reverse osmosis filter only passing water, a high pressure needs to be built up by pump 6, e.g. more than 10 bar, such as more than 25 Bar and sometimes still larger. This is adjusted by itself by the flows. The reason for needing such a high pressure in a reverse osmosis membrane is that the small ions that are excluded from passing membrane 9b will exert a high osmotic pressure which needs to be counteracted by pump 6 in order to pass water through the reverse osmosis membrane 9b. This also means that filter 9 must be constructed to withstand such high pressure as is known in the art.

Figure 6:
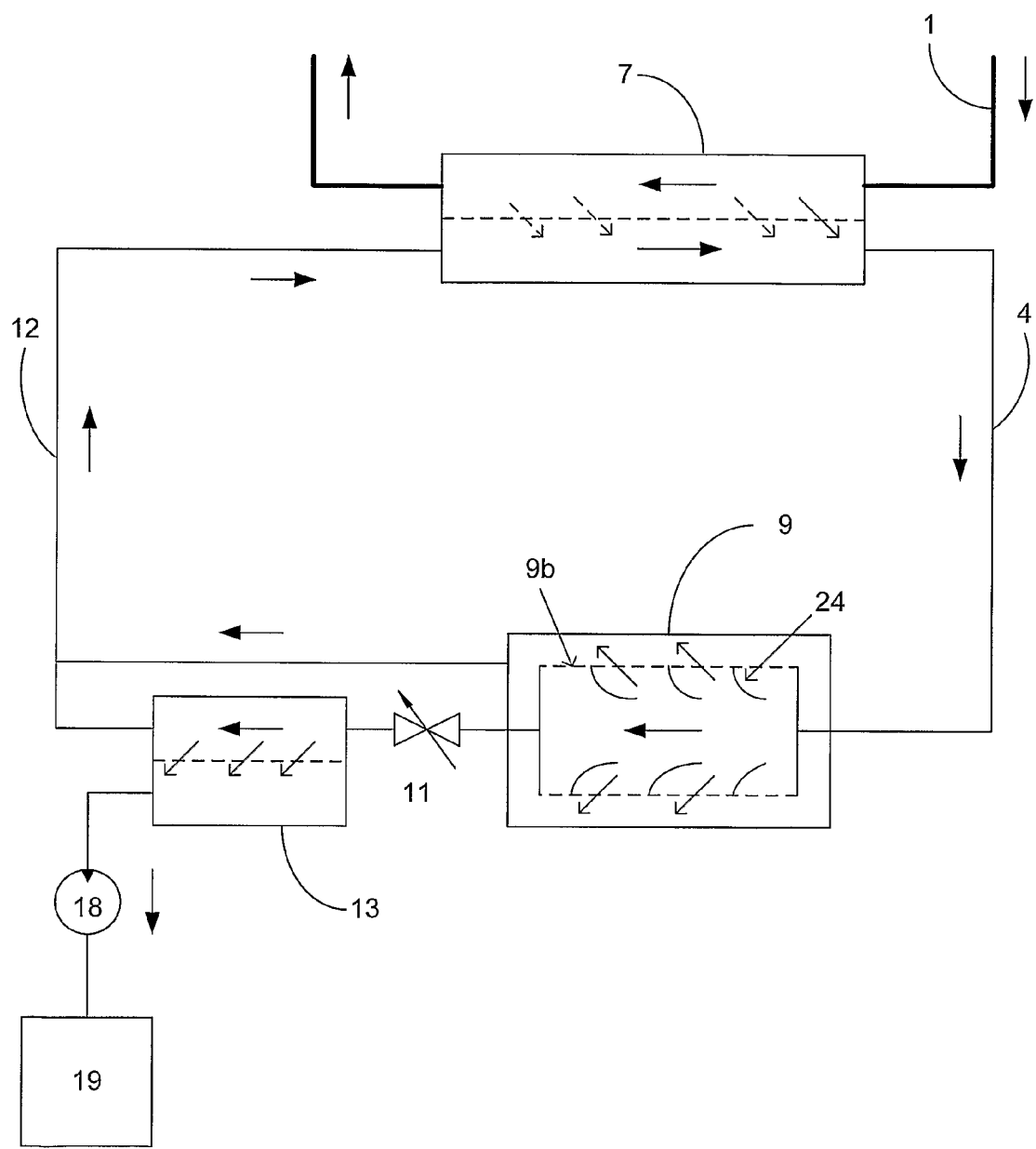
FIG. 6 is a schematic view of another embodiment, with a rotating reverse osmosis filter.
Figure 7:
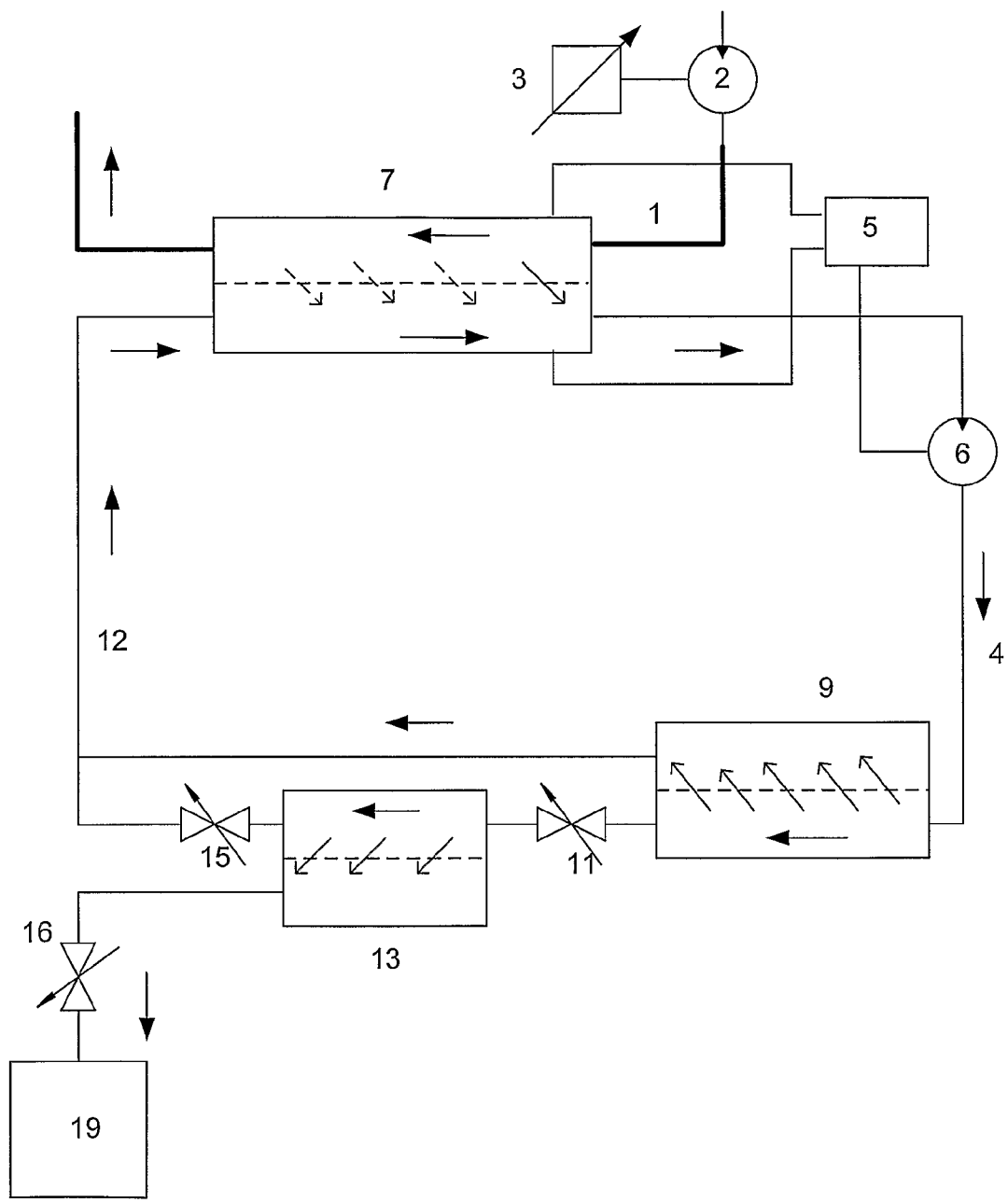
FIG. 7 is a schematic view of another embodiment.

In the embodiment shown in FIG. 5, the pumps 21 and 18 may be replaced by restrictions or throttles being adjustable to provide a suitable pressure drop. Thus, an adjustable throttle 11 may replace pump 21 for reducing the pressure from e.g. 25 bar to 1.5 bar, as shown in FIG. 6. A restriction 16 may replace pump 18 and is adjusted so that normally about 1 ml/min is passed to receptacle 19. In this case the only pump needed in the system is pump 6, as shown in FIG. 7.

A cylinder rotated by a high speed may generate the high pressure required to pass water through the reverse osmosis membrane 9b. Such an embodiment is shown in FIG. 6. The membrane 9b is arranged in the form of a cylinder, which is freely rotatable and driven by a motor (not shown). The dialysate fluid is entered into the cylinder via a central inlet and the retentate is passed out from the filter via a central outlet in the other end of the cylinder as shown in FIG. 6. The cylinder is provided with several fans 24 driving fluid in the longitudinal direction from the inlet to the outlet. When the cylinder is rotated, the dialysate fluid will follow the cylinder and be forced outward towards the semipermeable walls of the membrane. Centrifugal forces will develop counteracting the opposing osmotic pressure and water is flowing out through the membrane. The amount of water flowing out through the membrane is adjusted by the rotational speed of the cylinder. Consequently, the rotational speed of the cylinder controls the concentration ratio, which is desired for filter 9. The concentration ratio should be at least three, such as ten, for example fifteen. The retentate passed out from the reverse osmosis filter 9 via an adjustable throttle 11 to the separation filter 13. The permeate through the membrane of the separation filter is removed via pump 18 to receptacle 19. As before, a throttle may replace pump 18.

The concentration ratio is adjusted so that a desired removal of waste products is obtained. If the volume of the removed waste products is 1.5 l per day, and 750 mmoles urea should be removed per day, the concentration of urea in the retentate of RO filter 9 should be 500 mM. If the blood concentration of urea is about 50 mM and a complete equilibration of urea over the membrane in the dialyser 7 is obtained, a concentration ratio of ten should be used. The same concentration and removal is obtained for other small solutes such as NaCl and KCl. In the present case, and asuming the concentration of NaCl in blood is about 140 mM, a removal of 1.4 mole (82 g) of NaCl per day is obtained. For KCl having a concentration of about 4 mM in blood, about 40 mmole (3 g) is removed per day. These amounts can easily be replace by ingesting the corresponding amounts in the food products. If a concentration of urea in blood of 33 mM should be maintained, the pumps are adjusted so that a concentration of fifteen times takes place. Since the concentration filter is an RO filter, all substances in the retentate is concentrated by the same ratio, since only water passes through the membrane of an RO filter. The amount of urea to be removed per day depends on the urea generation rate of the patient, which is dependent on the protein intake and other factors.

The device should be provided with circuits monitoring the operation of the device. FIG. 7 discloses the embodiment of FIG. 1 provided with a central operating device 5 which controls the operation of pump 6 as well as the adjustable throttles 11, 15, 16 and pump 18, shown in FIG. 6. Moreover, the operating device 5 may include sensors connected to the dialyser 7 for monitoring the concentration of ions in the blood compartment and dialysate compartment of dialyser 7. Moreover, a pump 2 is shown operated by an adjustable actuator 3 for driving blood in the blood circuit. The operating unit 5 may control other parameters as well such as the blood pressure in the lines connecting to the patient, transmembral pressure, etc.

Figure 8:
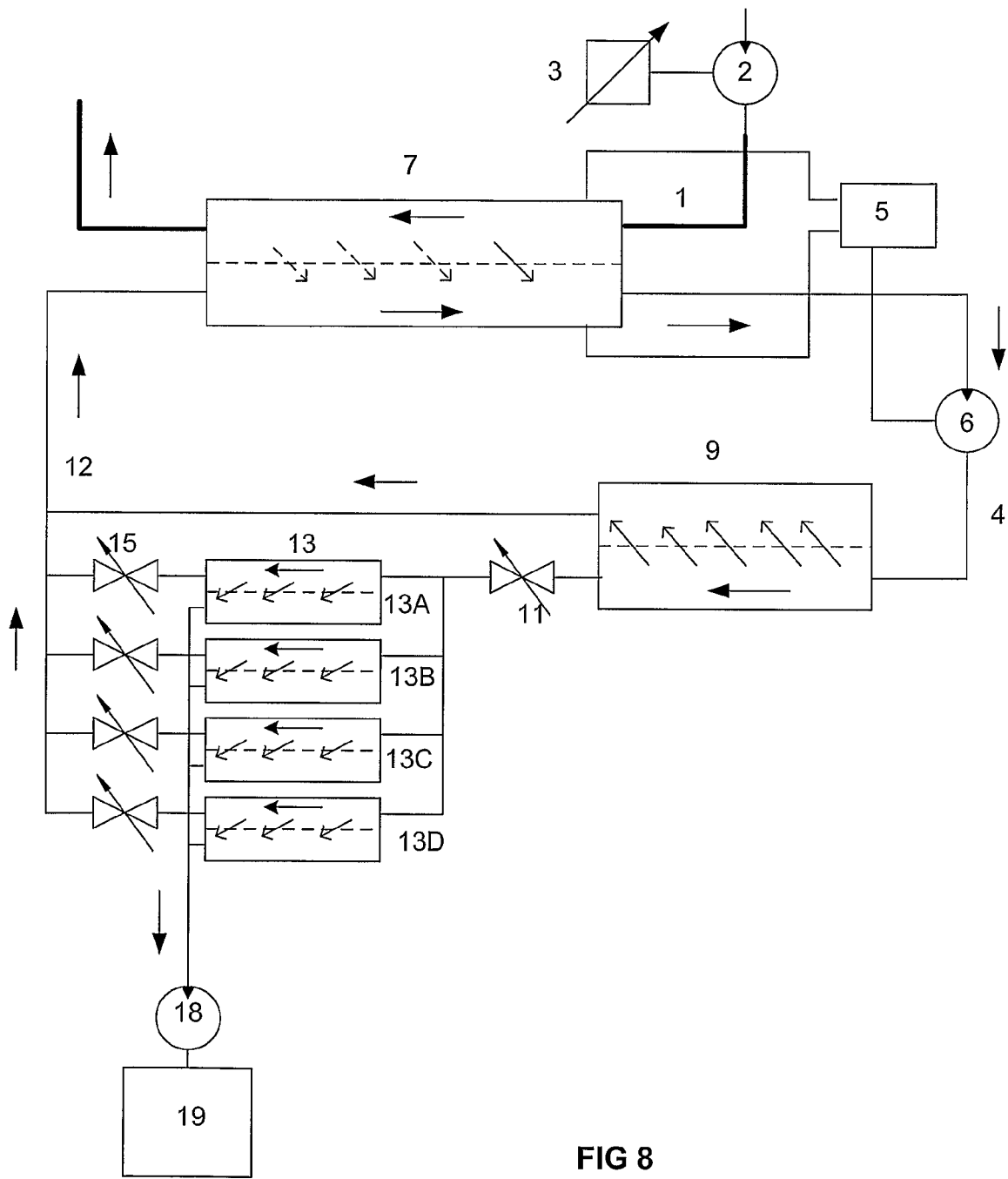
FIG. 8 is a schematic view of another embodiment, with several separation filters.

Another embodiment is shown in FIG. 8, which essentially corresponds to the embodiment of FIG. 7 except for that the separation filter is replaced by a filter system comprising four filter units. Each filter 13A, 13B, 13C, 13D are designed to pass a certain type of substances or ions. Thus, filter 13A may be a conventional filter having a size exclusion of about 100 D passing essentially urea and creatinine and smaller molecules and ions. Filter 13B may be a filter having electrical charges thereon for preventing ions from passing the filter but allowing non-charged particle to pass more easily. The membrane in the filter 13C may be a membrane having active transport of certain molecules, e.g. acid ions. Filter 13D may comprise a membrane having other properties. By combining these filters, a still better operation may be obtained.

Filters 13A-13D may be operated in sequence so that if one of the filters is contaminated or blocked, the next is connected.

Filters 13A-13D may as well be arranged in series instead of being arranged in parallel.

The membranes of the filters of the system may be finetuned to pass solutes and substances of different sizes. In an embodiment, the blood membrane passes only substances below about 1000 D from the blood to the dialysate. In another embodiment, a blood membrane having an exclusion limit of 100 D may be used. However, often a size exclusion limit of more than 10000 D up to 50000 D is desired for the blood membrane. Normally, larger size exclusion than 50000 D should be avoided loss of albumin from the blood.

The RO membrane of the RO filter should normally only pass water.

The separation membrane should permeate the waste products produced by the body, but retain important substances and ions or solutes, in order to prevent the excretion thereof. Some waste products are urea and creatinine. These products are not considered to be toxic per se, but serve as markers for other molucules that may be toxic and have the same molecular size as urea and creatinine. Since the waste products are produced by the body and are normally excreted by the kidney, such waste products will build up in the body if not removed by dialysis or some other process.

The products, which should not be removed by the system, are for example: $Na^+$, $K^+$, $Ca^{++}$, phosphate, glucose etc. It may be difficult to prevent the excretion of these products by the system. However, such excretion can be counteracted by the controlled addition of these products to the food ingested by the patients.

The size exclusion of the membranes may be the following: The blood membrane can be 100 D, 1000 D, 10000 D or 50000 D, depending on the desired result, as discussed above. The RO membrane should substantially only pass water. Some RO membranes also pass small amounts of other substances, such as sodium ions, which may be tolerated in the present system. The separation membrane should pass only small solutes and may be about 100 D.

The pressure drop over a membrane depends on the perforation ratio of the pores of the membrane. If a denser membrane is used, higher pressures are required in order to obtain operation of the system.

The membranes in the different filters mentioned may be selected based on different approaches. The filters may be any one of the types plate filters, spiral filters or hollow fibres as is conventional in the art. The membrane material can be any conventionally used material, such as cellulose-based, polyamide, polysulfon, polyethersulfon, polyacrylonitrile, etc.

Filter 7 may be used for a long time, since it is used continuously. Over the time, deposits, such as proteins adhering to the surface, will cover the inside of the membrane facing the blood. When such contaminations become too large, the filter has to be replaced.

A feature is that the dialysate is concentrated in the second filter 9 before being given off to receptacle 19. Thus, the operation of the human kidney is imitated and the fluid given off to receptacle 19 resembles that of urine.

Another feature is that no addition of a fluid is required during the operation of the system. The fluid is circulated and regenerated. The concentration of substances in the fluid takes place in dependence of the operation of the system and controlled by the respective pumps and membranes used in the system.

The fluid is kept sterile because no additions are performed. As soon as the system has been initiated, no further actions need to be taken to preserve sterility.

The apparatus includes only relatively small devices, which may be included in a small housing, which is easily wearable by a patient. Thus, the system may be used continuously, which means that the patient is not exposed to varying levels of waste products in the blood as is the fact in normal dialysis treatment. Consequently, the body will react positively and may be able to withstand the failing kidney function.

The system may be used with patients having still some residual kidney function whereby the kidney will be relaxed from a portion of its normal operation. Thus, the residual clearance of the partially still operating kidney supplements the removal by the system. There are some indications that the partially still operating kidney may maintain its operation over a longer period of time if supported by removal of some of the waste products, particularly if the level of waste product concentration in blood does not vary considerably.

The dialysis circuit can be initiated in different manners. One way would be to introduce sterile water in the system from the start. Pump 6 is operated very slowly so that the dialysate in the dialysis compartment of filter 7 will equilibrate with blood. The circulation continues until the entire dialysate has received approximately the same concentrations of ions as in blood. Then, the RO filter 9 is put into operation by increasing the pressure of pump 6 and restricting the throttle 11 so that a concentration takes place in the second filter 9. Finally, pump 18 is operated to remove the right amount of fluid from the system.

Alternatively, a dialysis fluid being preprepared with certain concentrations of ions may initiate the dialysis circuit. The dialysate fluid can be water having a physiological amount of salt, NaCl. Other substances may be added as well such as KCl, $NaHCO_3$, $CaCl_2$, etc.

The dialysate may be heated to a temperature close to the body temperature. However in some embodiments, no heating is required.

In the embodiment shown in FIG. 5, both urea and creatinine and small solutes such as $Na^+$, $K^+$, etc. will pass the separation membrane to the receptacle 19. However, the small solutes should remain in the dialysis circuit, if possible. However, the body is good in adapting itself to different removal of such small solutes and the body may easily adapt itself to this situation within a few days. Possibly, the intake of food has to be supplemented with addition of sodium and potassium salts.

The embodiments above have been described in an extracorporeal blood circuit. As mentioned before, the dialysator may as well be arranged inside the body, and more or less permanently connected to the blood vessels.

An alternative approach is to use an endogen membrane in place of the dialysator, such as the peritoneal membrane. The dialysis fluid is circulated into contact with the peritoneal membrane and then regenerated. Glucose or Dextros may be added for providing for fluid removal as is well known in peritoneal dialysis. The dialysis fluid may be entered into the peritoneal cavity and removed continuously for regeneration. Such removal may take place by two catheters or by a single dual-lumen catheter.

The fluid, such as dialysate, is circulated and an exchange of ions will take place over the peritoneal membrane. The transport of ions and substances is driven by the concentration gradient over the membrane, normally from the blood to the fluid. A small amount of fluid is also transported over the membrane.

As substances are transported over the membrane, an equilibration of the concentrations of these substances between the blood and the fluid will take place. Only the substances, which are sufficiently small to pass the membrane, will be equilibrated, while molecules having a size, which is larger than the pores of the membrane, will be maintained in the blood.

Figure 10:
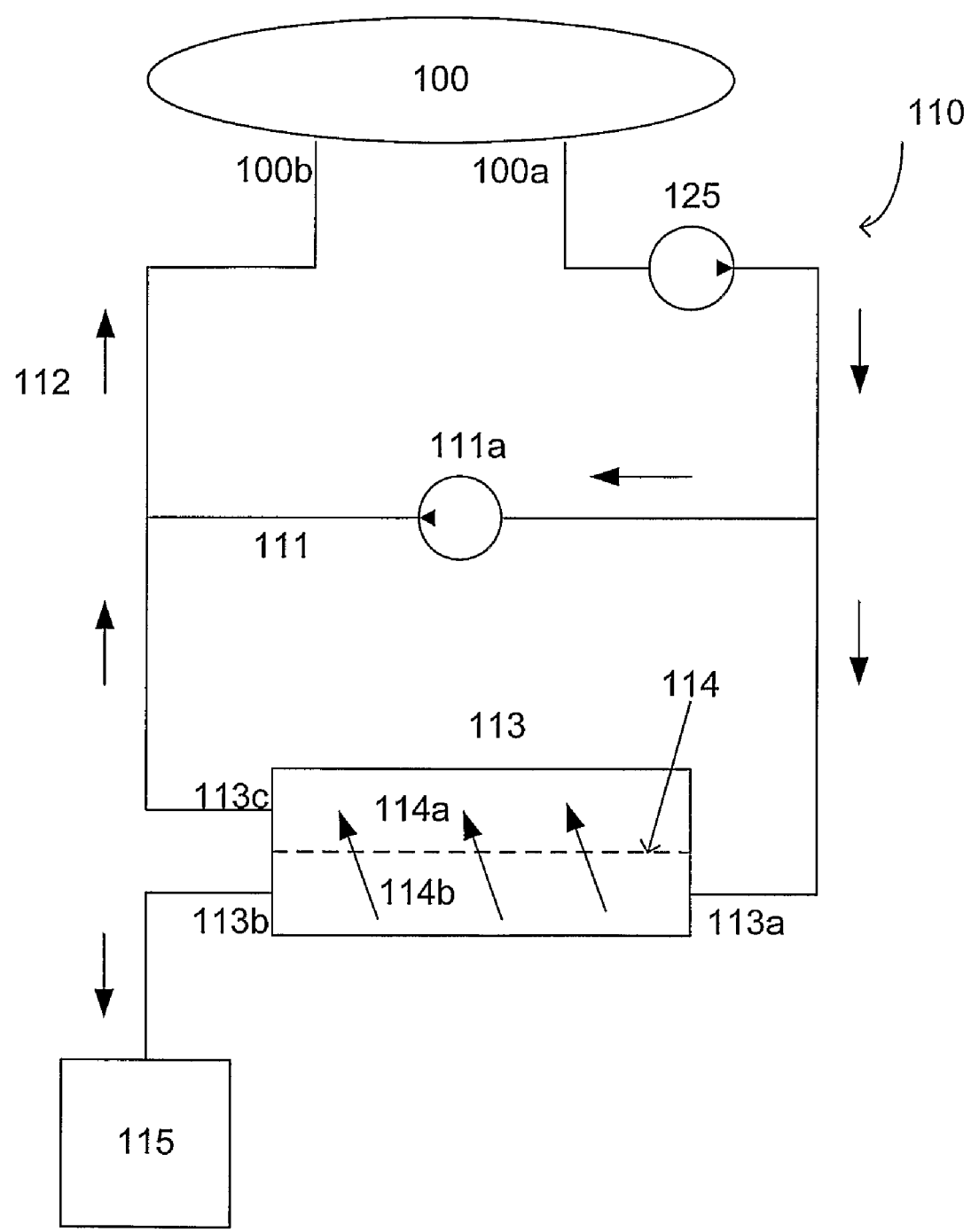
FIGS. 10-12 are schematic views of embodiments using the peritoneal membrane of a patient and an reverse osmosis filter.

FIG. 10 shows an embodiment of a system specifically adapted for regeneration of a fluid included in the peritoneal cavity of a mammal, such as a human being to be treated. The peritoneal fluid comprises an osmotically active agent for withdrawing fluid from the blood via the peritoneal membrane. Such an agent may be glucose, but can alternatively be Dextran or another molecule exhibiting osmotic or colloidal-osmotic activity. Dextran is a molecule that can be produced with different molecular weight. In the present context, a dextrane molecule having a molecular weight of about 40000 D may be used. This molecule is hardly absorbed by the body through the peritoneal membrane and produces a substantial osmotic effect resulting in withdrawal of water to the peritoneal fluid. The peritoneal fluid may include other solutes, such as NaCl, KCl, $CaCl_2$, etc as is well-known in the art. Since the Dextran molecule is slowly absorbed by the body, the peritoneal fluid is exchanged when the concentration of the Dextran molecule has decreased below a certain level. Such exchange may take place each day or each week.

The peritoneal dialysis circuit includes a volume of fluid positioned in the peritoneal cavity of the patient as indicated by the compartment 100. The regeneration system shown in FIG. 10 regenerates this fluid.

The fluid is withdrawn from compartment 100 and one part of the fluid passes bypass line 111 and one part of the fluid enters the RO filter 113 in a first compartment 114*a*. Filter 113 is arranged as an reverse osmosis (RO) filter, which means that fluid enters the filter by an inlet 113*a* to a first compartment 114*b*, and leaves the filter as a retentate fluid through an outlet 113*b* and as a permeate fluid (water) through an outlet 113*c* after passing the filter membrane 114 as indicated by arrows. The filter membrane is a membrane having very small pores and essentially only passing water. The retentate fluid is collected in a receptacle 115.

The permeate fluid of filter 113 is returned to the compartment 100, i.e. peritoneal cavity, via line 112. The fluid is driven in the regeneration circuit by suitable pumps 125, 111*a* or throttles as will be described in further detail below.

Figure 11:
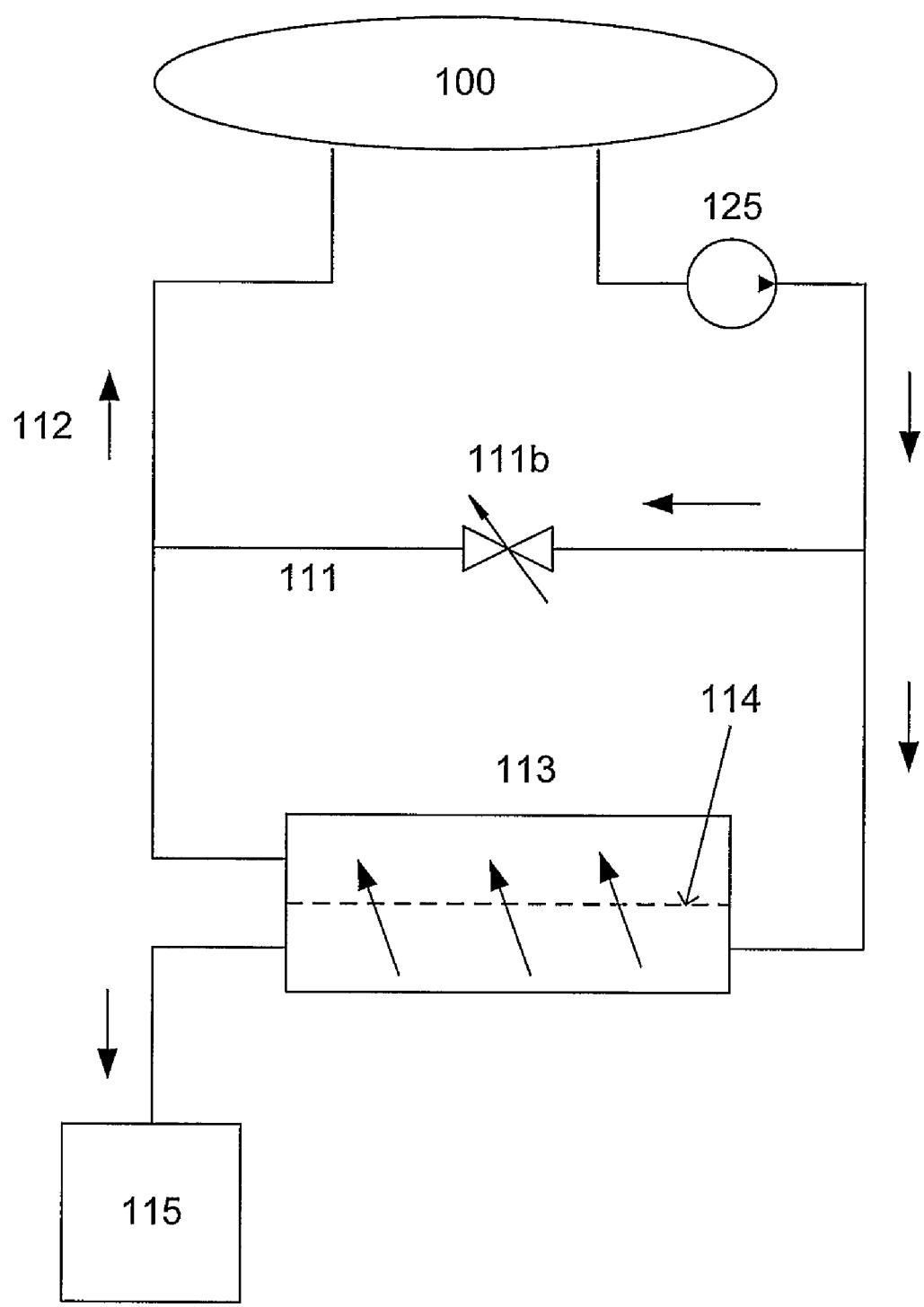
Figure 12:
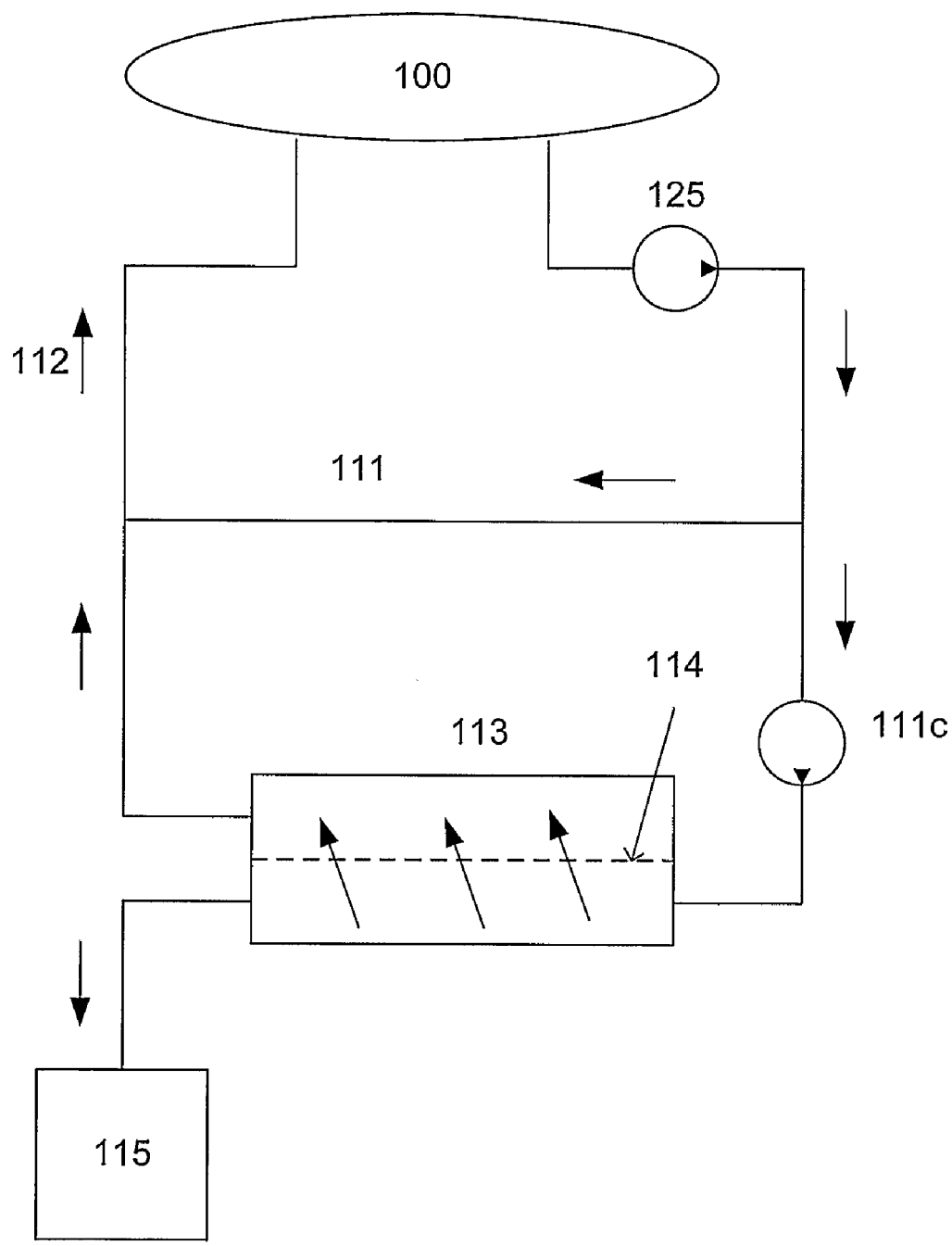

The operation of the fluid circuit of FIG. 10 is as follows: Waste products and other small substances and/or ions in the blood passes through the peritoneal membrane into the fluid in the peritoneal cavity 110. The fluid is circulated into the bypass line 111 or into the second filter 113, the ratio is controlled by the pump 125 in combination with the pump 111*a*, as shown in FIG. 10, the throttle 111*b* as shown in FIG. 11, or the pump 111*c* as shown in FIG. 12. The fluid, which is circulated into the RO filter, is concentrated since essentially only water passes through the RO membrane 114. The concentrated fluid or retentate fluid is passed to the receptacle 115. The water or permeate of the RO filter is returned to the peritoneal cavity 110. In this way, the fluid entering the peritoneal cavity 110 will have a low content of particularly urea and creatinine that has been separated by filter 113.

Figure 13:
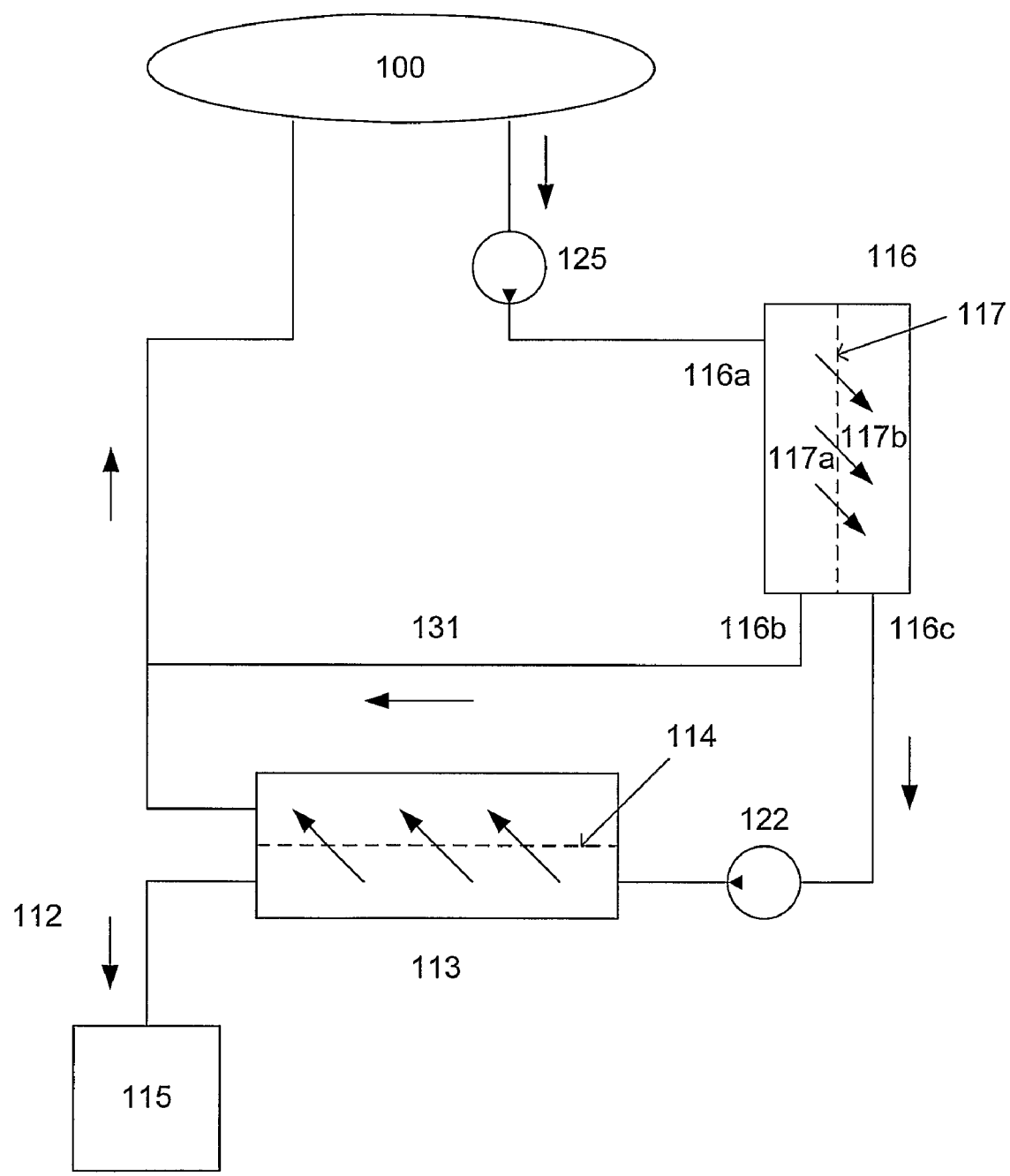
FIG. 13 is a schematic view of another embodiment, with a nanofilter.

In another embodiment, shown in FIG. 13, the fluid circuit is arranged as a nanofiltration treatment. In this case, a separation filter 116, a nanofilter (NF), is placed before the RO filter. This means that fluid enters the first compartment 117*a* and fluid passes through the membrane 117 of the filter into the second compartment 117*b*. The retentate is returned to the peritoneal cavity 110 via line 131 and the permeate is passed on to the RO filter 113 for concentration. Only ions having a size smaller than the exclusion size of the membrane in the separation filter is passed on to the RO filter. This order of the filters may be used in the other embodiments as well.

The operation of the system of FIG. 13 is as follows: The fluid is circulated into the separation filter 116. One part of the fluid passes the membrane 117, as controlled by the pumps 125 and 122, and further, as permeate, into the RO filter, where it is concentrated. The other part or retentate, which comprises all substances and ions that cannot pass the separation membrane is returned to the peritoneal cavity via line 131 and line 112.

The concentrated fluid or retentate of the RO filter is passed to the receptacle 115 and the permeate of the second filter is returned to the peritoneal cavity 110. In this way, the fluid entering the peritoneal cavity 110 will have a low content of particularly urea and creatinine that has been separated by filter 116 and concentrated by filter 113.

The separation membrane is dimensioned so that the retentate comprises the osmotically active agent, such as glucose or Dextran, which should remain in the circuit and should not be excreted to the receptacle 115. Thus, the osmotically active agent is preserved as much as possible, which results in that the peritoneal fluid needs to be exchanged more seldom. The peritoneal fluid excerts its osmotic activity and withdraws fluid from the blood when firstly introduced into the peritoneal cavity, thus increasing its volume during the first hours. The body, partly depending on the fact that the osmotically active agent is absorbed, then slowly reabsorbs the fluid. The slower the osmotically active agent is absorbed, the longer the peritoneal fluid can remain in the body for removing other waste products. Since such other waste products are removed continuously according to this embodiment, fluctuations in the blood concentration of such waste products can be avoided.

Figure 14:
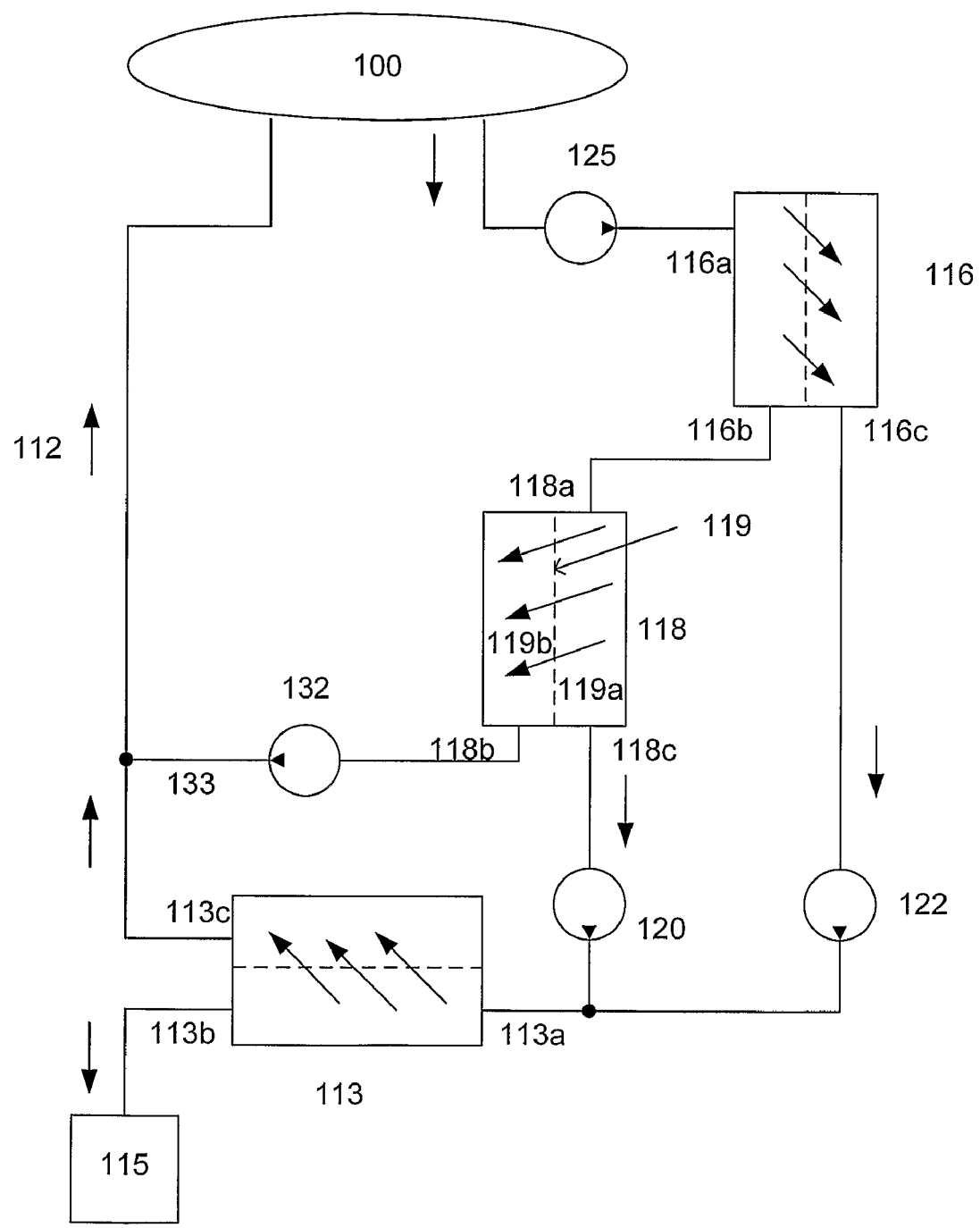
FIG. 14 is a schematic view of another embodiment, with an ultrafilter.

In a further embodiment, shown in FIG. 14, the system further comprises an ultrafilter 118 (UF), arranged between the separation filter and the RO filter. The retentate from the separation filter, which comprises the osmotically active agent, enters the first compartment 119a of ultrafilter 118 and fluid passes through a membrane 119 into the second compartment 119b. The permeate is returned to the compartment 100 via line 133 and the retentate is passed to the RO filter 113.

The operation of the system of FIG. 14 is as follows: The fluid is circulated into the ultrafilter 118. One part of the fluid passes the membrane 119 and the amount is controlled by the pumps 125, 120 and 132, and further, as permeate, returned to the peritoneal cavity 100 via line 133. The other part or retentate is passed into the RO filter, where it is concentrated. The concentrated fluid or retentate of the RO filter is passed to the receptacle 115 and the permeate of the RO filter is returned to the peritoneal cavity 110. In this way, the fluid entering the peritoneal cavity 110 will have a low content of particularly urea and creatinine that has been separated by filter 118.

The ultrafilter membrane is dimensioned so that it may pass the osmotically active agent but retain larger molecules or substances, so called middle molecules. In this way, middle molecules are excreted to the receptacle 115 as controlled by pump 120, while small molecules are excreted as controlled by pump 122.

Figure 15:
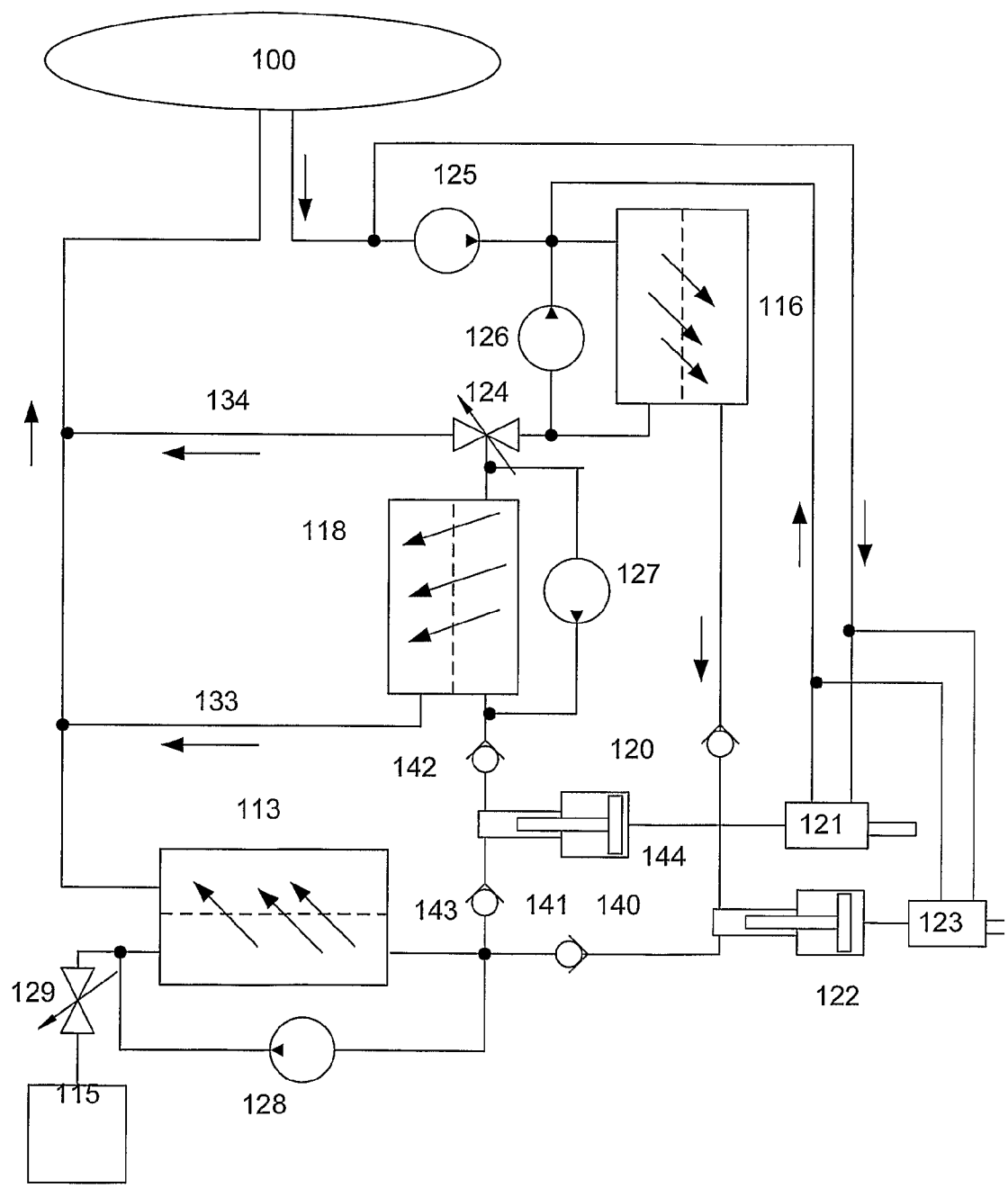
FIG. 15 is a schematic view of another embodiment, with a pump system.

FIG. 15 shows the embodiment according to FIG. 14 including pumps for operating the flows in the fluid circuit.

The RO filter must be operated at a high pressure to pass only water through the membrane because of the high osmotic counter-pressure. In the embodiment shown in FIG. 15, a pressure amplifier provides the high pressure, for example a piston type pressure amplifier as shown in FIG. 15.

Such a pressure amplifier or pump comprises a piston 140 having a small area at a drive side, to the left in FIG. 15, and a large area at en operation side, to the right in FIG. 15. The fluid to be pressurized is connected to a small area cylinder 141 via a non-return valve 142 and introduced in the cylinder 141. When the cylinder is full, a pressure fluid is applied to a large area cylinder 144 acting on said piston 140 and urging the fluid in the small area cylinder 141 out from the cylinder via another non-return valve 143 at a pressure which is amplified by the ratio of the piston areas.

The pressure fluid may be obtained from a pump in the system, such as pump 125 in FIG. 15. The pressure over pump 125 may for example normally be about 3 bar and the ratio between the piston surfaces may be nine to provide an amplified pressure of up to 27 bar.

A valve 121 directs said pressure fluid to the large area cylinder 144 of the piston upon activation of the valve, resulting in that the fluid in the small area cylinder is expelled at a pressure of up to 27 bar.

When all fluid in the cylinder has been expelled, the valve 121 is reversed and the fluid in the large cylinder is relieved via valve 121 at the same time as new fluid enters the small cylinder, and the process is repeated.

A throttle 124 may be arranged to redirect the retentate fluid directly from the separation filter to the dialysate circuit via line 134 in the case when ultrafiltration is not desired.

The additional pumps 126, 127 and 128 are used for increasing the tangential flow of the fluid over the membrane of respective filter in order to counteract clogging of the filter. The direction of flow can be any direction, such as counterflow as shown in connection with the separation filter 116 and pump 126 or concurrent flow as shown in connection with the ultrafilter 118 and pump 127.

The extracorporeal system may alternatively be operated intermittently.

The system has no control of acidity, which normally is performed by the kidney. Consequently, the patient may need to take in sodium bicarbonate or similar substances orally. If the kidney has a residual function, such function may be sufficient for acidity control of the blood.

Figure 9:
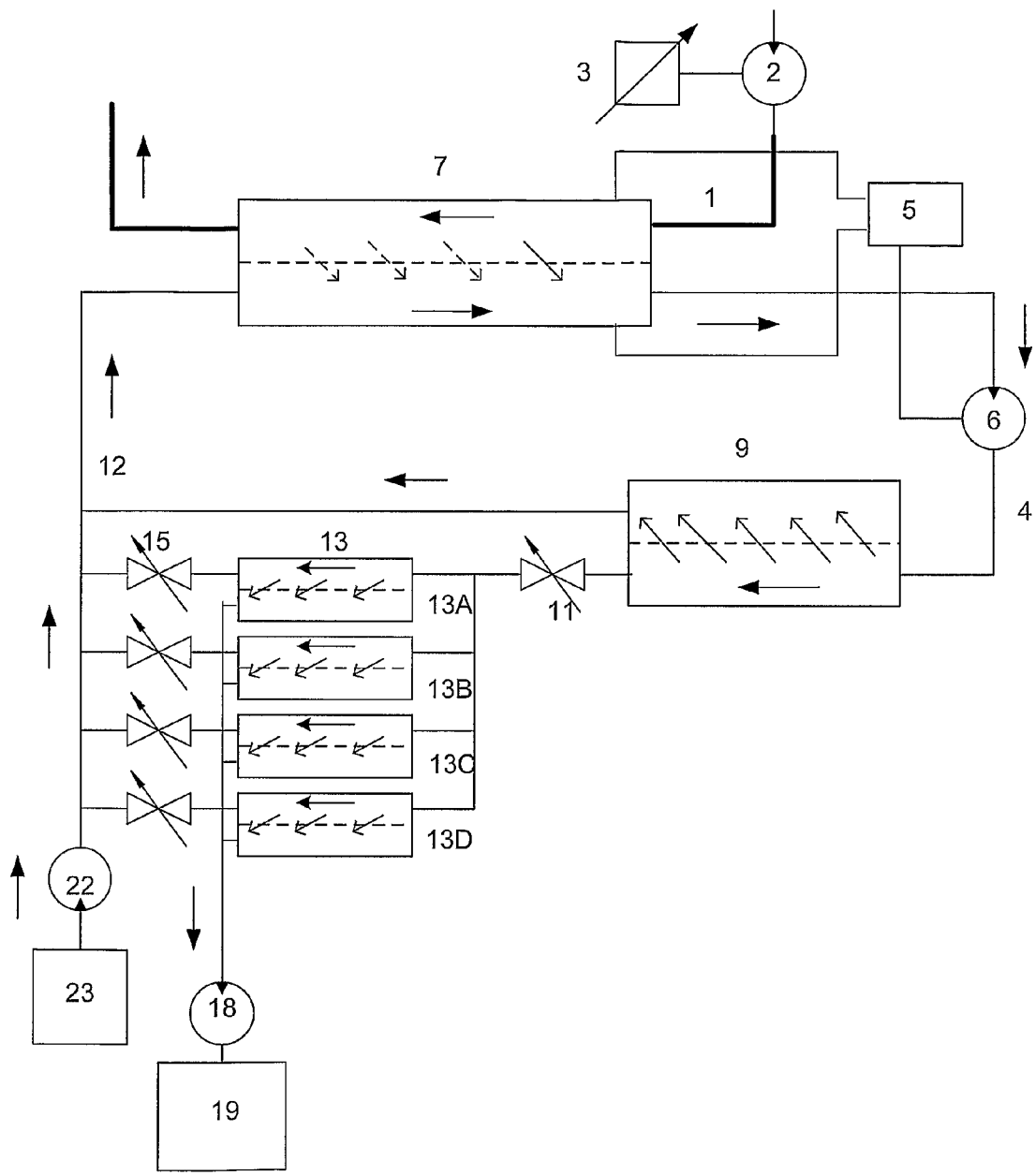
FIG. 9 is a schematic view of another embodiment, with addition of a substance.

Alternatively, the system may be provided with the possibility of adding certain substances to the dialysis circuit as shown in FIG. 9. Such addition may be sodium bicarbonate. Other additions may be sodium and potassium ions. The substances may be contained in a receptacle 23 in a very concentrated form and they could be infused into the dialysis circuit by a pump 22. Such substances can alternatively be taken in orally. In the case of peritoneal dialysis, the substance may be the osmotically active agent, such as glucose or Dextran.

The invention has been described above with reference to several embodiments comprising separate features. However, such features may be combined in other manner than explicitly described in connection with each embodiment. The third filter in FIG. 1 may be arranged before the RO filter as shown in FIG. 13. The invention is not limited by the embodiments described, but only by the appended patent claims.

The invention claimed is:

1. A system for regeneration of a fluid included in a compartment and being in contact with blood via a membrane comprising:
   a device for providing said fluid from said compartment to a reverse osmosis filtering device for filtering substantially only water from said fluid for providing a concentrated fluid;

a separating filter for removing at least a portion of said concentrated fluid; and a device for returning the non-removed portion and said water as said regenerated fluid to said compartment and/or directly to the blood, wherein no fluid is added into the system from outside.

2. The system according to claim 1, wherein said concentrated fluid of said reverse osmosis filtering device is concentrated at least in a ratio of 3 to 1.

3. The system according to claim 1, wherein said compartment is the abdominal cavity of a patient and said membrane is a peritoneal membrane in the abdominal cavity.

4. The system according to claim 1, wherein the separating filter is connected to the retentate outlet of said reverse osmosis filtering device, whereby a retentate fluid of said separating filter is returned to said compartment and a permeate fluid of said separating filter is removed from the system as a waste fluid.

5. The system according to claim 4, wherein said separating filter is a filter system comprising at least two separating membranes.

6. The system according to claim 4, wherein said device for providing said fluid from said compartment to said reverse osmosis filtering device is a first pump;

wherein said device for returning the non-removed portion and said water as said regenerated fluid to said compartment and/or directly to the blood is a second pump for passing a retentate fluid from said reverse osmosis filtering device to said separating filter; and wherein the system further comprises a third pump for passing the permeate fluid from the separating filter to a receptacle as a waste fluid.

7. The system according to claim 4, wherein said device for providing said fluid from said compartment to said reverse osmosis filtering device is a first pump;

wherein said device for returning the non-removed portion and said water as said regenerated fluid to said compartment and/or directly to the blood is an adjustable valve for passing a retentate fluid from said reverse osmosis filtering device to said separating filter; and wherein the system further comprises a second pump for passing the permeate fluid from said separating filter to a receptacle as a waste fluid.

8. The system according to claim 1, further comprising:

a port arranged in a blood circuit including said membrane and compartment, said port being connected for passing at least a portion of said regenerated fluid into the blood circuit before said compartment, so called predilution.

9. The system according to claim 1, further comprising:

a port arranged in a blood circuit including said membrane and compartment, said port being connected for passing at least a portion of said regenerated fluid into the blood circuit after said compartment, so called postdilution.

10. The system according to claim 1, wherein said concentrated fluid of said reverse osmosis filtering device is concentrated at least in a ratio of 10 to 1.

11. The system according to claim 1, wherein said concentrated fluid of said reverse osmosis filtering device is concentrated at least in a ratio of 15 to 1.

* * * * *